United States Patent
Yahng et al.

(10) Patent No.: US 10,222,204 B2
(45) Date of Patent: Mar. 5, 2019

(54) HIGH-SPEED 3D IMAGING SYSTEM USING CONTINUOUS-WAVE THZ BEAM SCAN

(71) Applicant: KOREA RESEARCH INSTITUTE OF STANDARDS AND SCIENCE, Daejeon (KR)

(72) Inventors: Ji Sang Yahng, Daejeon (KR); Dae-Su Yee, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 0 days.

(21) Appl. No.: 15/291,630

(22) Filed: Oct. 12, 2016

(65) Prior Publication Data
US 2017/0102231 A1 Apr. 13, 2017

(30) Foreign Application Priority Data
Oct. 13, 2015 (KR) .................. 10-2015-0142906

(51) Int. Cl.
*G01B 11/25* (2006.01)
*G01B 11/24* (2006.01)
(Continued)

(52) U.S. Cl.
CPC .......... *G01B 11/2518* (2013.01); *G01B 11/24* (2013.01); *G01N 21/3586* (2013.01);
(Continued)

(58) Field of Classification Search
CPC ................................................. G01B 11/2518
See application file for complete search history.

(56) References Cited

U.S. PATENT DOCUMENTS

2009/0283680 A1* 11/2009 Logan, Jr. ............. G01J 3/10
250/339.07
2011/0163234 A1 7/2011 Cluff
(Continued)

FOREIGN PATENT DOCUMENTS

| JP | 2009-8658 | 1/2009 |
|---|---|---|
| JP | 2012-90690 | 5/2012 |
| KR | 10-1453472 | 10/2014 |

OTHER PUBLICATIONS

Jin, Kyong Hwan. et al., "High-speed terahertz reflection threedimensional imaging for nondestructive evaluation," 1Department of Bio and Brain Engineering, Korea Advanced Institute of Science and Technology, Daejeon, South Korea, Optics Express vol. 20, No. 23, Oct. 25, 2012.
(Continued)

*Primary Examiner* — Hugh H Maupin
(74) *Attorney, Agent, or Firm* — Hauptman Ham, LLP (57) ABSTRACT

Provided is a high-speed 3D imaging system using continuous-wave THz beam scan, and more particularly, a high-speed 3D imaging system using continuous-wave THz beam scan capable of acquiring a 3D image for a sample at a high speed and high precision by measuring a signal reflected from a sample using the continuous-wave THz beam generated from a wavelength-fixed laser and a wavelength-swept laser and having a frequency varying at a high speed to obtain depth direction information on a sample and performing a 2D scan on the sample using a THz beam scanner.

10 Claims, 6 Drawing Sheets

(51) Int. Cl.
G02B 13/00 (2006.01)
G02B 26/10 (2006.01)
G02B 27/10 (2006.01)
G01N 21/3586 (2014.01)

(52) U.S. Cl.
CPC ....... G02B 13/0005 (2013.01); G02B 26/105 (2013.01); G02B 27/106 (2013.01); G02B 27/1006 (2013.01)

(56) References Cited

U.S. PATENT DOCUMENTS

| | | | |
|---|---|---|---|
| 2011/0192978 A1 | 8/2011 | Jeon et al. | |
| 2016/0135891 A1* | 5/2016 | Feldman | A61B 5/0066 606/3 |
| 2016/0320170 A1* | 11/2016 | Yun | A61B 5/0059 |

OTHER PUBLICATIONS

Yahng, Ji Sang, et al., "High-Speed Frequency-Domain Terahertz Coherence Tomography," Korea Research Institute of Standards and Science, Daejeon, South Korea, 2015 IEEE, 978-1-4799-8272-1.
Yee, Dae-Su, et al., "High-Speed Broadband Frequency Sweep of Continuous-Wave Terahertz Radiation" Korea Research Institute of Standards and Science, Daejeon, South Korea, 2015 IEEE, 978-1-4799-8272-1.
Yahng Ji Sang et al.; "High-speed frequency-domain terahertz coherence tomography", 2015 40th International Conference on Infrared, Millimeter, and Terahertz Waves (IRMMW-Thz), IEEE, Aug. 23, 2015 (Jun. 23, 2015), DOI: 10.1109 IRMMW-THZ.2015.7327781.

* cited by examiner

HIGH-SPEED 3D IMAGING SYSTEM USING CONTINUOUS-WAVE THZ BEAM SCAN

CROSS-REFERENCE TO RELATED APPLICATIONS

This application claims priority under 35 U.S.C. § 119 to Korean Patent Application No. 10-2015-0142906, filed on Oct. 13, 2015, in the Korean Intellectual Property Office, the disclosure of which is incorporated herein by reference in its entirety.

TECHNICAL FIELD

The following disclosure relates to a high-speed 3D imaging system using continuous-wave THz beam scan, and more particularly, to a high-speed 3D imaging system which may scan an imaging target using a continuous-wave THz beam, which is generated from a wavelength-fixed laser and a wavelength-swept laser and of which the frequency is changed at a high speed, to obtain a 3D image for the imaging target at a high speed in a non-destructive and non-contact way.

It is very important and essential to measure a shape of a sample in technical fields of the industries. As a result, various research and developments for a technology of measuring a shape of a sample have been actively conducted. For example, in case of a 2D image measuring technology for measuring micro shapes of a 2D plane such as measuring a line width of a semiconductor integrated circuit or inspecting a pattern defect, foreign materials, asymmetry, etc., a probe system using image pick-up devices such as an optical microscope and a CCD camera is representative. A technology of acquiring a 2D image has been already commercialized in the fields of a general optical microscope or electron microscope and widely used.

Meanwhile, as a need for acquisition of information on a 3D shape as well as a 2D image is increased, a technology of measuring a 3D shape of a surface of a sample or an internal shape of the sample as well as an appearance of the sample has also been evolved in various ways. As an example of the technology, there are a technology of imaging and detecting an in vivo 3D structure, a technology of discriminating an object in a vessel, a technology of detecting cracks in a sample, etc. For this purpose, the sample needs to be measured by the non-destructive way. Additionally, if the sample is measured by the non-contact way, the measurement result would be even better.

BACKGROUND

Among non-destructive and non-contact detection technologies, a technology of acquiring a projection image is simplest. As an example of the technology, there is an X-ray technology, etc. As known well, in case of irradiating a transmittable electromagnetic wave, the X-ray to the sample and then detecting the X-ray transmitting the sample, the detected amount of X-ray varies depending on the absorbed amount of X-ray while the X-ray transmits the 3D sample. On this basis, it is possible to obtain a 2D projection image for the 3D sample.

A terahertz (THz) beam is also an electromagnetic wave having excellent transmission and may transmit various non-conductive materials such as fiber and plastic. In particular, compared to the X-ray, the terahertz beam has relatively lower photon energy and thus does not harm a biological tissue or DNA, thereby obtaining higher biological safety. A non-destructive inspection technology using a THz beam may be used in a security check to check stuffs in a suitcase or whether passengers possess weapons, etc.

Meanwhile, the projection image acquired by using the X-ray or the THz beam as described above may provide only the 2D information on the 3D object. As a technology of more accurately exposing a 3D structure for a sample, a computed tomography (CT) technology, an optical coherence tomography (OCT) technology, or the like have been used. Generally, these technologies have been mostly used to image an in vivo 3D structure in a medical field. In the CT technology, tomographic or 3D images may be reconstructed by obtaining X-ray projection images for a sample at multiple angles and then recombines the images. Further, the OCT technology uses an optical coherence phenomenon to image micro structures in a sample. In particular, the OCT technology may image micro structures in a biological tissue while minimizing a damage to the biological tissue, and as a result has been in the limelight of a medical field.

By the way, as generally well known, the CT technology needs to obtain hundreds to thousands of 2D projection images for a sample at different angles, and therefore it takes much time to obtain a CT image. That is, a 3D shape detection technology using the CT method requires a too long image acquisition time to be applied to industries other than the medical field. Meanwhile, in the OCT technology, researches for improving a light source output, stability, a speed, etc., have been actively conducted. However, since a 3D imaging depth is only several mm, the OCT technology may be restrictively applied to a retinal diagnosis, an endoscope technology, or the like.

Today, a necessity for a 3D imaging technology is growing in various industries. However, as described above, the technologies that have been developed and used currently have rather limitations due to specialties that have been studied to meet characteristics of the respective technical fields and therefore have trouble in applying to more various industries. An example of the problems to be solved by the 3D imaging technology that may be applied to more various industries may include detecting more various samples by reducing a limitation on a material, a size, or the like. Above all, what is most urgent for the 3D imaging technology is to implement the high-speed and high-precision measurement.

Among the foregoing technologies, the imaging technology using the THz beam may acquire a 3D image by being combined with other technologies. Compared to the X-ray CT technology, the imaging technology using the THz beam does not damage a sample and therefore has higher safety and compared to the OCT technology, the imaging technology using the THz beam may detect a sample having a much larger depth, and so on. That is, the THz beam may have several characteristics that may be appropriately used for a next generation high-speed 3D imaging technology. However, researches for the imaging technology using the THz beam are still in beginning stages, and therefore the imaging technology using the THz beam has many problems to be solved.

A method for obtaining a 3D image using a THz beam is classified into a transmission type and a reflection type. The transmission type is similar to the foregoing CT technique. However, the transmission type uses the THz beam instead of using the X-ray, and therefore may have high biological safety but still has a problem of too long measurement time that is the largest problem with the CT technology. The reflection type uses a time-of-flight (TOF) principle. That is, the reflection type calculates a distance based on the returning time of beam when the beam is irradiated to a sample and reflected from the sample to acquire information in a depth direction (that is, beam propagation direction). The THz beam has properties of reflection at interfaces as well as transmission, and therefore the reflection type may calculate a position where a reflected signal is generated by detecting the reflected signal to understand position information on the interfaces present in a depth direction of a sample and investigate the depth direction information on multiple points on a 2D plane perpendicular to the depth direction, thereby acquiring the 3D shape information in the sample.

Figure 1:
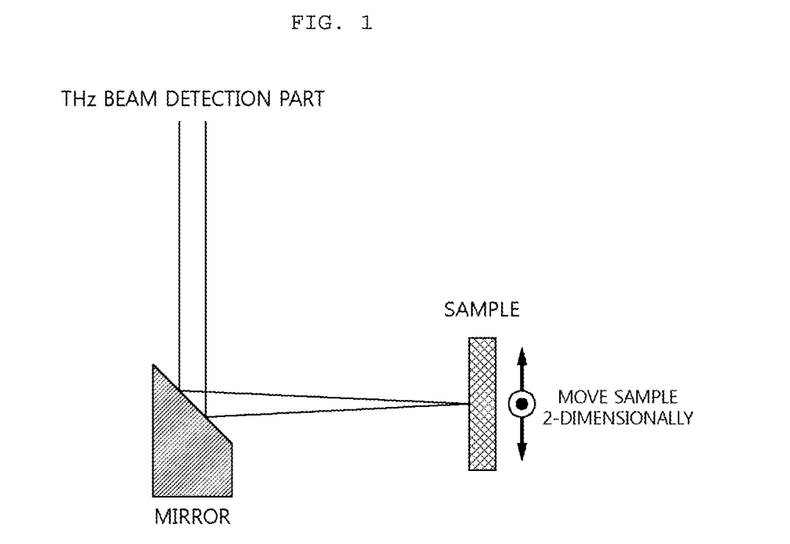
FIG. 1 is a diagram schematically illustrating the existing imaging system using a THz beam according to the related art.

FIG. 1 is a diagram schematically illustrating the existing reflection type 3D imaging system using a THz beam, in which the 3D imaging system irradiates the THz beam to a sample to acquire a reflected signal and moves the sample two-dimensionally. In more detail, a detailed content thereof is disclosed in "High-speed terahertz reflection three-dimensional imaging for nondestructive evaluation" (Kyong Hwan Jin, Young-Gil Kim, Seung Hyun Cho, Jong Chul Ye, Dae-Su Yee, 25 Nov. 2012/Vol. 20, No. 23/OPTICS EXPRESS, hereinafter, related art document 1).

As described in the related art document 1, the reflection type 3D imaging system may detect the high-precision 3D image using the THz beam, and as a result achieve considerable technical development in the 3D imaging technical fields. However, since the sample needs to be physically moved on the 2D plane, the reflection type 3D imaging system disclosed in the related art document 1 still has a limitation in speed and precision. As a result, there is a need to increase the speed. In addition, as described in the related art document 1, the reflection type 3D imaging system uses the pulse wave THz beam to measure the reflected signal in the time domain and therefore needs to use femtosecond pulse lasers to generate and measure the pulse wave THz beam. As a result, the reflection type 3D imaging system may have a problem in that it takes much cost to configure the imaging system and it is difficult to miniaturize the system.

As the related art document disclosing a method for generating a terahertz continuous-wave, of which the frequency varies at a high speed, using a wavelength-fixed laser and a wavelength-swept laser, there is Korean Patent No. 10-1453472. However, the method suggests simply a technology generating a terahertz continuous-wave of which the frequency varies at a high speed and does not yet suggest a technology of measuring a 3D image using the generated terahertz continuous-wave.

RELATED ART DOCUMENT

Non-Patent Document

1. "High-speed terahertz reflection three-dimensional imaging for nondestructive evaluation" (Kyong Hwan Jin, Young-Gil Kim, Seung Hyun Cho, Jong Chul Ye, Dae-Su Yee, 25 Nov. 2012/Vol. 20, No. 23/OPTICS EXPRESS)

Patent Document

1. Korean Patent No. 1453472 (Published on Oct. 21, 2014)

SUMMARY

An object of the present invention is directed to providing a high-speed 3D imaging system capable of using continuous-wave THz beam scan to acquire a 3D image for a sample at a high speed and high precision. Another object of the present invention is directed to providing a high-speed 3D imaging system using continuous-wave THz beam scan, which may be advantageous in saving costs and miniaturization, by applying the continuous-wave THz beam to the high-speed 3D imaging system using the THz beam scan.

In one general aspect, a high-speed 3D imaging system using continuous-wave THz beam scan includes: a wavelength-fixed laser 1 generating first laser light having a first fixed wavelength; a wavelength-swept laser 2 generating second laser light having a second wavelength varying from a preset minimum wavelength to a preset maximum wavelength at a high speed for one period; a coupler 4 coupling the first laser light with the second laser light to form mixed light and splitting the mixed light into first mixed light and second mixed light; an emitter 5 receiving the first mixed light split from the coupler 4 to output a continuous-wave THz beam having a frequency corresponding to a difference between a frequency corresponding to a first wavelength and a frequency corresponding to a second wavelength; a detector 7 receiving the second mixed light split from the coupler 4 and the THz beam reflected from a sample 11 to generate the photocurrent; a beam splitter 8 disposed in a propagation path of the THz beam emitted from the emitter 5 to pass the THz beam emitted from the emitter 5 and reflect the THz beam reflected from the sample 11 to make the THz beam incident on the detector 7; a galvanometer scanner 9 receiving the THz beam emitted from the emitter 5 to adjust a direction angle of the THz beam; a telecentric f-θ lens 10 irradiating the THz beam of which the angle is adjusted by the galvanometer scanner 9 toward the sample 11; a digital pulse generator 12 generating a trigger signal with a signal at a specific wavelength of the wavelength-swept laser 2; a first waveform signal generator 15 applying a voltage to the emitter 5 based on the generated trigger signal; a 2D scan driver S controlling an angle adjustment of the galvanometer scanner 9 based on the generated trigger signal; a digitizer 13 digitalizing a reflected signal of the THz beam detected by the detector 7 and an angle adjustment driving signal of the galvanometer scanner 9 based on the generated trigger signal; and a computer 14 receiving the digitalized reflected signal of the THz beam and the digitalized angle adjustment driving signal from the digitizer 13 to obtain 3D shape information on the sample 11 by analyzing the reflected signal of the THz beam to obtain depth information on a shape of the sample 11 and analyzing the angle adjustment driving signal to obtain information on 2D position on the sample 11 from which the reflected signal of the THz beam is generated.

The wavelength-swept laser 2 may have a wavelength sweep rate that is a value ranging from hundreds of Hz to hundreds of kHz and the one period of the wavelength-swept laser 2 may be a reciprocal number of the wavelength sweep rate.

The 2D scan driver S may include: a second waveform signal generator 16 generating a waveform signal for driving the galvanometer scanner 9 based on the trigger signal generated from the digital pulse generator 12; and at least one rotation driver 17 and 18 using the driving waveform signal received from the second waveform signal generator 16 to rotate the galvanometer scanner 9.

The high-speed 3D imaging system using continuous-wave THz beam scan may further include: a semiconductor optical amplifier or an optical fiber amplifier 3 for amplifying the first laser light or the second laser light.

The digitizer 13 may digitalize the reflected signal of the THz beam detected by the detector 7 for one period that is the reciprocal number of the wavelength sweep rate, based on the trigger signal of the same frequency as the wavelength sweep rate generated from the digital pulse generator 12, in digitalizing the reflected signal of the THz beam.

To improve a signal to noise ratio of the reflected signal of the THz beam, the first waveform signal generator may apply a bias voltage alternately and repeatedly turned on/off based on the trigger signal generated from the digital pulse generator 12 to the emitter 5, the digitizer 13 may repeatedly digitize the reflected signal of the THz beam for the one period and provide the digitalized reflected signal to the computer 14, and the computer 14 may alternately add, subtract, and average the repeatedly acquired digital data.

The high-speed 3D imaging system using continuous-wave THz beam scan may further include: a variable time delay tool 6 variably time-delaying the first mixed light split from the coupler 4 and inputting the variably time-delayed first mixed light to the emitter 5 or variably time-delaying the second mixed light and inputting the variably time-delayed second mixed light to the detector 7.

The high-speed 3D imaging system using continuous-wave THz beam scan may further include: an amplifier 19 amplifying a signal detected by the detector 7 and transferring the amplified signal to the digitizer 13.

The high-speed 3D imaging system using continuous-wave THz beam scan may further include: at least one off-axis parabolic mirror or lens 20 used to collimate the THz beam emitted from the emitter 5 or focus the THz beam reflected from the beam splitter 8 on the detector 7.

The high-speed 3D imaging system may be configured of a head in which the emitter 5, the detector 7, the beam splitter 8, the off-axis parabolic mirror or lens 20, the galvanometer scanner 9, and the telecentric f-θ lens 10 are integrally unitized and the optical fiber-coupled emitter and detector may be used as the emitter 5 and the detector 7 and thus the head may be portably formed.

Other features and aspects will be apparent from the following detailed description, the drawings, and the claims.

[Detailed Description of Main Elements]

| | |
|---|---|
| 1: Wavelength-fixed laser | 2: Wavelength-swept laser |
| 3: Semiconductor optical amplifier or optical fiber amplifier | |
| 4: Coupler | |
| 5: Emitter | 6: Variable time delay tool |
| 7: Detector | 8: Beam splitter |
| 9: Galvanometer scanner | 10: Telecentric f-θ lens |
| 11: Sample | 12: Digital pulse generator |
| 13: Digitizer | 14: Computer |
| 15: First waveform signal generator | |

-continued

[Detailed Description of Main Elements]

| | |
|---|---|
| 16: Second waveform signal generator | |
| 17, 18: Rotational driver | 19: Amplifier |
| 20: Off-axis parabolic mirror or lens | |
| S: 2D scan driver | |

DETAILED DESCRIPTION OF EMBODIMENTS

Hereinafter, a high-speed 3D imaging system using continuous-wave THz beam scan according to an exemplary embodiment of the present invention having the foregoing configuration will be described with reference to the accompanying drawings.

THz Beam Scan Principle

Figure 2:
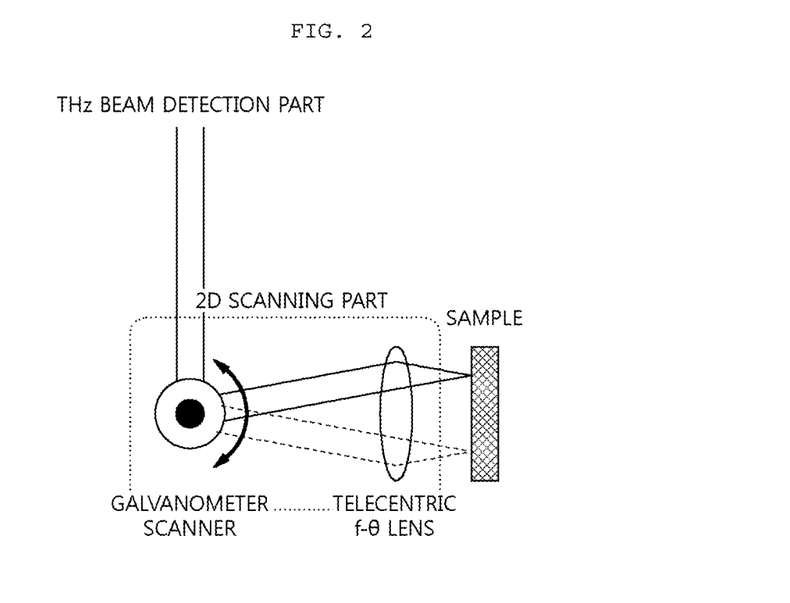
FIG. 2 is a schematic diagram for describing a THz beam scan principle.

FIG. 2 is a schematic diagram for describing a THz beam scan principle. The relate art illustrated in FIG. 1 moves a sample two-dimensionally to perform a 2D scan, and therefore has a limitation of improving a measurement speed or precision. According to an exemplary embodiment of the present invention, to increase a speed of a 3D image detection using a THz beam, a 2D scan is performed by scanning the THz beam instead of moving a sample two-dimensionally.

The system schematically illustrated in FIG. 2 includes a THz beam detection part and a 2D scanning part. The THz beam detection part serves to detect a reflected signal by irradiating the THz beam to the sample and reflecting the THz beam from the sample and the 2D scanning part serves to adjust a 2D position where the THz beam is irradiated to the sample. Hereinafter, a schematic principle of calculating depth information while performing the 2D scan with the 2D scanning part will be described intensively and a generation and a detection of the THz beam will be again described in separate sections later.

The detection of the depth information using reflection of the THz beam is based on the following principle. First, if the THz beam is irradiated to the sample, the THz beam is transmitted inside the sample in case that a refractive index of a material forming the sample is uniform, but is reflected from an interface where the refractive index is changed. In this case, the depth information on the interface where the THz beam is reflected may be calculated by measuring a time delay of the reflected signal of the THz beam.

In this case, according to the exemplary embodiment of the present invention, the 2D scanner includes a galvanometer scanner adjusting a direction angle of the THz beam and a telecentric f-θ lens irradiating the THz beam of which the angle is adjusted by the galvanometer scanner toward the sample. The telecentric f-θ lens is a lens that allows incident rays to have a constant direction and a focal distance independent of an angle.

The existing imaging system using the THz beam illustrated in FIG. 1 is configured to directly move physically the sample itself using a translation stage in a two-dimensional direction, such that it may have a problem in that a 2D scan speed of the sample is limited. However, according to the exemplary embodiment of the present invention, as illustrated in FIG. 2, the 2D position of the THz beam irradiated to the sample is adjusted by adjusting the direction angle of the THz beam using the galvanometer scanner, and therefore there is no need to directly move the sample. As known well, the galvanometer scanner is an apparatus configured to rotate a small mirror depending on an applied voltage. In this case, since the mirror to be moved is small and light and therefore a moment generation is reduced, high-speed and high-precision driving is facilitated. That is, the translation stage in which the sample to be detected is mounted is relatively large and heavy, and therefore the driving of the galvanometer scanner may be performed at a higher speed and higher precision than physically moving the sample to be detected.

As described above, a direction angle of the THz beam may be appreciated based on a rotation driving signal value of the galvanometer scanner. As described above, a two-dimensional position of the THz beam on a focal plane is determined based on an angle of incident rays on the telecentric f-θ lens. That is, if the sample is positioned on the focal plane of the telecentric f-θ lens, the 2D position of the THz beam on the sample may be easily understood based on the rotation driving signal value of the galvanometer scanner.

How to calculate 3D shape information on the sample by the so configured system according to the exemplary embodiment of the present invention will be described below in more detail. When a medium forming the sample is uniform, the THz beam will be reflected from a top (surface) of the sample and a bottom (floor) of the sample. If the THz beam is irradiated to any one point (x1 and y1) position on 2D of the sample, when a reflected signal reflected from the top of the sample has a time delay of Δt11 and a reflected signal reflected from the bottom of the sample has a time delay of Δt12, a distance value (that is, depth information) z11 corresponding to the Δt11 and a distance value (that is, depth information) z12 corresponding to the Δt12 may be calculated. That is, it may be appreciated from the result of measuring the reflected signal having the two time delay values (in this example, Δt11 and Δt12) that the sample at the point (x1, y1) has the top at the position z11 in the depth direction and the bottom at the position z12.

In another case, when the THz beam is irradiated to another point (x2 and y2) position on the 2D, reflected signals having four different time delay values are measured. In this case, depth information values calculated by each time delay value are assumed to be z21, z22, z23, and z24. That is, this means that a material through which the THz beam is transmitted and propagated is changed at the position (x2, y2) four times, that is, there are four interfaces. In detail, the z21 becomes the depth information on the top of the sample and the z24 becomes the depth information on the bottom of the sample and the z22 and z23 become the depth information on the top and bottom interfaces of any other material (for example, crack) that is present within the sample at the (x2, y2) position.

As such, the depth information (z11 and z12, etc.) on the sample at any 2D position may be calculated based on the THz beam detector and the 2D position values (x1 and y1, etc.) may be calculated based on a rotation driving signal value of the galvanometer scanner as described above. That is, a 3D shape of the sample may be completely reconfigured by acquiring the depth information values (z11 and z12, etc.) of the interfaces present at a plurality of points (x1 and y1, etc.) on the 2D and putting together these depth information values.

Detailed Example of High-Speed 3D Imaging System Using Continuous-Wave THz Beam Scan According to the Present Invention As described above, the depth direction information on the respective 2D points is acquired by collecting time delay data simultaneously with two-dimensionally scanning the THz beam using the galvanometer scanner and the telecentric f-θ lens and the 3D image information may be acquired by putting together the acquired depth direction information.

As described above, a pulse wave THz beam or a continuous-wave THz beam may be used as the THz beam to measure the 3D image. For using the pulse wave THz beam, a femtosecond pulse laser needs to be used and therefore cost may be increased. If the continuous-wave THz beam is used to measure the 3D image, cost may be reduced. However, data need to be measured while changing the frequency of the continuous-wave THz beam to obtain the depth direction information, and therefore it takes much time to measure.

According to the exemplary embodiment of the present invention, as described above, the system may be economically configured by using the continuous-wave THz beam as the THz beam used for the 3D image detection simultaneously with realizing the high-speed 3D image detection by two-dimensionally scanning the THz beam and the depth direction information may be acquired at a high speed despite the use of the continuous-wave THz beam.

According to the exemplary embodiment of the present invention, as one laser of the two lasers used to generate the continuous-wave THz beam, a wavelength-swept laser is used. In this case, the depth direction information is obtained by a method different from the method for using a pulse wave THz beam as described above. In summary, the high-speed 3D imaging system according to the exemplary embodiment of the present invention measures the frequency-domain data at a high speed while changing the frequency of the continuous-wave THz beam at a high speed, thereby obtaining the depth direction information based on signal processing.

Figure 3:
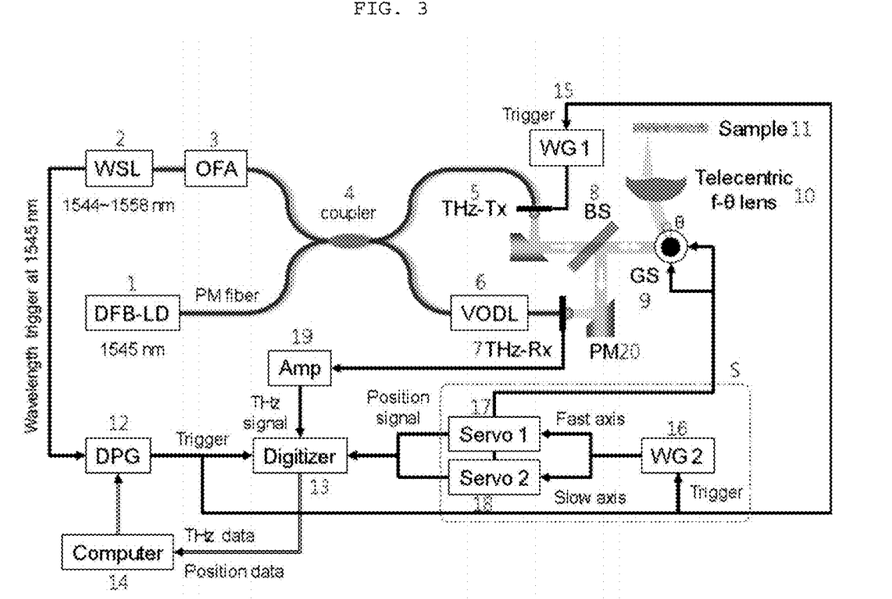
FIG. 3 is a diagram illustrating a high-speed 3D imaging system using continuous-wave THz beam scan according to an exemplary embodiment of the present invention.

FIG. 3 is a diagram illustrating a detailed example of a high-speed 3D imaging system using continuous wave THz beam scan according to an exemplary embodiment of the present invention. The high-speed 3D imaging system according to the exemplary embodiment of the present invention may basically include a wavelength-fixed laser 1, a wavelength-swept laser 2, a coupler 4, a generator 5, a detector 7, a beam splitter 8, a galvanometer scanner 9, a telecentric f-θ lens 10, a digital pulse generator 12, a first waveform signal generator 15, a 2D scan driver S, a digitizer 13, and a computer 14. The basic components will be described below in more detail and additional apparatuses may be further provided to the components to improve various functions.

The wavelength-fixed laser 1 generates first laser light having a first fixed wavelength. The wavelength-fixed laser may be a distributed feedback laser diode (DFB-LD). To obtain the continuous-wave THz beam of a wide frequency band, it is preferable to fix the first wavelength to be close to a threshold value (minimum value or maximum value) in a varying section of a second wavelength. In detail, when the varying section of the second wavelength ranges from 1544 nm to 1558 nm, the first wavelength may be 1545 nm.

The wavelength-swept laser 2 generates second laser light having the second wavelength changed at a high speed. When the optical power of the first laser light or the second laser light is low, a semiconductor optical amplifier or an optical fiber amplifier 3 may be preferably provided to amplify the first laser light or the second laser light. Further, the wavelength-swept laser 2 may preferably have a wavelength sweep rate that is a value ranging from hundreds of Hz to hundreds of kHz and one period of the wavelength-swept laser 2 is represented by a reciprocal number of the wavelength sweep rate.

Here, the range of the wavelength sweep rate will be described below in more detail. Basically, the higher the wavelength sweep rate, the faster the measurement speed of the high-speed 3D imaging system of the present invention. However, considering a signal to noise ratio of a combination of a generator and a detector of the current level of technology, the wavelength sweep rate may appropriately range from hundreds of Hz to several kHz. An experiment of the present invention (to be described below in more detail) was also performed in the above range. The current wavelength-swept laser already realized the wavelength sweep rate of hundreds of kHz. When the generator and detector technology was more evolved in the future to increase the signal to noise ratio enough to operate the wavelength sweep rate of the wavelength-swept laser at hundreds of kHz, the measurement speed may be more improved. Further, the wavelength-swept laser technology is more evolved, and thus the laser having the wavelength sweep rate higher than the existing hundreds of kHz may also be developed and used. As described above, the higher the wavelength sweep rate the faster the measurement. Therefore, the present invention describes that the wavelength sweep rate may adopt hundreds of kHz, but is not limited thereto. That is, considering the technical development of the respective apparatuses as described above, the wavelength sweep rate is adopted as the highest level that may be implemented by the technical level at that time. In fact, a limitation of an upper bound of the wavelength sweep rate is of little significance.

The coupler 4 may couple the first laser light with the second laser light to form mixed light and split the mixed light into first mixed light and second mixed light.

The generator 5 may convert the first mixed light split from the coupler 4 into the THz beam. When the generator 5 is a photomixer, the generator 5 may include a photoconductor and an antenna. When a bias voltage of the first waveform signal generator 15 is applied to the generator 5, the photoconductor converts the mixed light into a photocurrent, in which the photocurrent may be emitted as the continuous-wave THz beam through the antenna. The generator 5 may use a beat phenomenon to generate the continuous-wave THz beam having a frequency corresponding to a difference between a frequency corresponding to a first wavelength and a frequency corresponding to a second wavelength. Therefore, the frequency of the THz beam determined by the first fixed wavelength and the second wavelength varying at a high speed may vary at a high speed. A frequency sweep rate of the THz beam is equal to the wavelength sweep rate of the wavelength-swept laser 2 and a frequency sweep period that represents a reciprocal number of the frequency sweep rate of the THz beam is equal to the a wavelength sweep period that represents a reciprocal number of the wavelength sweep rate of the wavelength-swept laser 2. The sweep rate may range from hundreds of Hz to hundreds of kHz. For example, if the sweep rate of the second wavelength is 1 kHz, the sweep period may be 1 ms.

The second mixed light split from the coupler 4 and the THz beam reflected from the sample 11 are input to the detector 7 and photocarriers excited by the second mixed light may be biased by an electric field of the THz beam in the detector 7 to generate the photocurrent. When the time delay is excessively increased due to a difference between lengths of the two optical paths from the coupler 4 to the detector 7, coherence between the THz beam and the second mixed light may be reduced in the detector 7. Therefore, the time delay may be appropriately adjusted by using a variable time delay tool 6 which may time-delay the first mixed light or the second mixed light to keep the coherence between the THz beam and the second mixed light in the detector 7. Here, the high-speed 3D imaging system may include an amplifier 19 which amplifies the photocurrent output from the detector 7 and transfers the amplified photocurrent to the digitizer 13.

The beam splitter 8 is disposed in a propagation path of the THz beam emitted from the generator 5 to serve to pass the THz beam emitted from the generator 5 and reflect the THz beam reflected from the sample 11 and make the THz beam be incident on the detector 7. As illustrated in FIG. 3, the THz beam emitted from the generator 5 is irradiated to the sample 11 through the galvanometer scanner 9 and the telecentric f-θ lens 10 to be described below and the optical path is changed so that the beam reflected from the sample 11 is incident on the detector 7 by the beam splitter 8.

The digital pulse generator 12 generates a trigger signal from a signal at a specific wavelength of the wavelength-swept laser 2 to set a time reference for the operation of the apparatus and the information calculation to be described below. In this case, the specific wavelength may be 1545 nm.

The digitizer 13 serves to digitalize the reflected signal of the THz beam detected by the detector 7 and an angle adjustment driving signal of the 2D galvanometer scanner 9 based on the trigger signal generated from the digital pulse generator 12. Here, the reflected signal of the THz beam means a detection signal generated from the detector 7 by the reflected THz beam, not the reflected THz beam itself. Describing in more detail the digitalization of the reflected signal of the THz beam, the digitizer 13 digitalizes the reflected signal of the THz beam detected by the detector 7 for one period, based on the trigger signal of the same frequency as the wavelength sweep rate generated from the digital pulse generator 12. In this case, one period represents the reciprocal number of the wavelength sweep rate.

Further, the high-speed 3D imaging system is operated as follows to improve the signal to noise ratio of the reflected signal of the THz beam. That is, first, the first waveform signal generator 15 applies a bias voltage alternately and repeatedly turned on/off based on the trigger signal generated from the digital pulse generator to the generator 5 and the digitizer 13 repeatedly digitalizes the reflected signal of the THz beam for one period and provides the digitalized reflected signal to the computer 14. (The computer 14 performs an operation of receiving and processing the signals transferred from several apparatuses, which will be described below in more detail.) Then, the computer 14 alternately adds, subtracts, and averages the repeatedly acquired digital data, thereby improving the signal to noise ratio.

The galvanometer scanner 9 receives the THz beam emitted from the generator 5 to adjust the direction angle of the THz beam and the telecentric f-θ lens 10 serves to irradiate the THz beam of which the angle is adjusted by the galvanometer scanner 9 toward the sample 11. Further, the 2D scan driver S serves to control the angle adjustment of the galvanometer scanner 9 based on the generated trigger signal The angle of the galvanometer scanner 9 is adjusted by the 2D scan driver S to change the 2D irradiation position of the THz beam. As a result, it takes a predetermined time to acquire the depth information at any one position on the 2D. That is, a process of staying the THz beam at any one position on the 2D for a predetermined time and then moving the THz beam to another position on the 2D to stay at the position needs to be repeated. In this case, the timing when the THz beam is fixed at any position on the 2D or moved to another position is determined based on the trigger signal generated from the digital pulse generator 12.

The 2D scan driver S, that is, a part for driving the galvanometer scanner 9 may include a second waveform generator 16 generating a driving waveform signal based on the trigger signal generated from the digital pulse generator 12 and at least one rotation driver 17 and 18 using the driving waveform signal received from the second waveform signal generator 16 to rotate the galvanometer scanner 9.

For the 2D scan, two mirrors included in the galvanometer scanner 9 are each driven to rotate. That is, the THz beam is reflected to the two mirrors in the galvanometer scanner 9 in order to be incident on the telecentric f-θ lens 10 and the position on the 2D is determined by the angle of the two mirrors. In this case, the two rotation drivers 17 and 18 rotate the two mirrors in the galvanometer scanner 9, respectively. In more detail, one of the two mirrors in the galvanometer scanner 9 is rotated fast and the other thereof is rotated slowly, thereby performing a raster scan.

The computer 14 serves to receive the digitalized reflected signal of the THz beam and the digitalized angle adjustment driving signal from the digitizer 13 to obtain 3D shape information on the sample 11 by analyzing the reflected signal of the THz beam to obtain depth information on a shape of the sample 11 and analyzing the angle adjustment driving signal to obtain information on 2D position on the sample 11 from which the reflected signal of the THz beam is generated. This will be described below in more detail.

First, the computer 14 receives the digitalized reflected signal of the THz beam from the digitizer 13 to generate frequency-domain data, performs fast Fourier transform on the frequency-domain data to generate time-domain data, and calculates the depth information on the shape of the sample 11 based on the time-domain data. Further, the computer receives the digitalized angle adjustment driving signal from the digitizer 13 to calculate the information on the 2D position on the sample 11 where the reflected signal of the THz beam is generated. The computer 14 puts together the obtained depth information and information on the 2D position to calculate the 3D shape information of the sample 11. As described above, the trigger signal is generated at the moment that the wavelength-swept laser 2 is a specific wavelength and the generator 5, the digitizer 13, and the galvanometer scanner 9 are operated based on the trigger signal, such that an operation reference of all parts is set based on the trigger signal of the digital pulse generator 12.

Additional Components

The high-speed 3D imaging system using continuous wave THz beam scan according to the exemplary embodiment of the present invention configured as described above may use a THz beam scanner including the galvanometer scanner 9 and the telecentric f-θ lens 10 to perform a scan in the 2D direction (C-scan) at a high speed as illustrated and use the wavelength-swept laser 2 of which the wavelength varies at a high speed to perform a scan in a depth direction (A-scan) at a high speed, thereby realizing the high-speed 3D scan.

In addition, the amplifier 19 is further provided on a signal transfer path between the detector 7 and the digitizer 13 so that the reflected signal of the THz beam detected by the detector 7 may be more smoothly recognized while the reflected signal is transferred to the digitizer 13. Here, the amplifier 19 amplifies the signal detected by the detector 7, that is, the reflected signal of the THz beam and transfers the amplified reflected signal to the digitizer 13.

Further, as illustrated, at least one off-axis parabolic mirror or lens 20 may be further provided on the THz beam path. The off-axis parabolic mirror or the lens 20 is basically used to collimate and focus the THz beam. In more detail, the off-axis parabolic mirror or the lens is provided on the THz beam path emitted from the generator 5 to collimate the THz beam or the off-axis parabolic mirror or the lens 20 is provided on the THz beam path reflected from the beam splitter 8 to focus the THz beam on the detector 7.

Meanwhile, the high-speed 3D imaging system is configured of a head in which the generator 5, the detector 7, the beam splitter 8, the off-axis parabolic mirror or lenses 20, the galvanometer scanner 9, and the telecentric f-θ lens 10 are integrally unitized. That is, the listed components are configured in one head when an actual system is configured, and as a result the system may be easily miniaturized and commercialized. Further, the optical fiber-coupled generator and the detector are used as the generator and the detector, such that the head may be portably formed.

Principle of Calculating Depth Direction Information Based on Reflected Signal of THz Beam Hereinafter, the principle of calculating, by the digitizer, the depth direction information based on the digitalized reflected signal of the THz beam will be described.

Figure 4A:
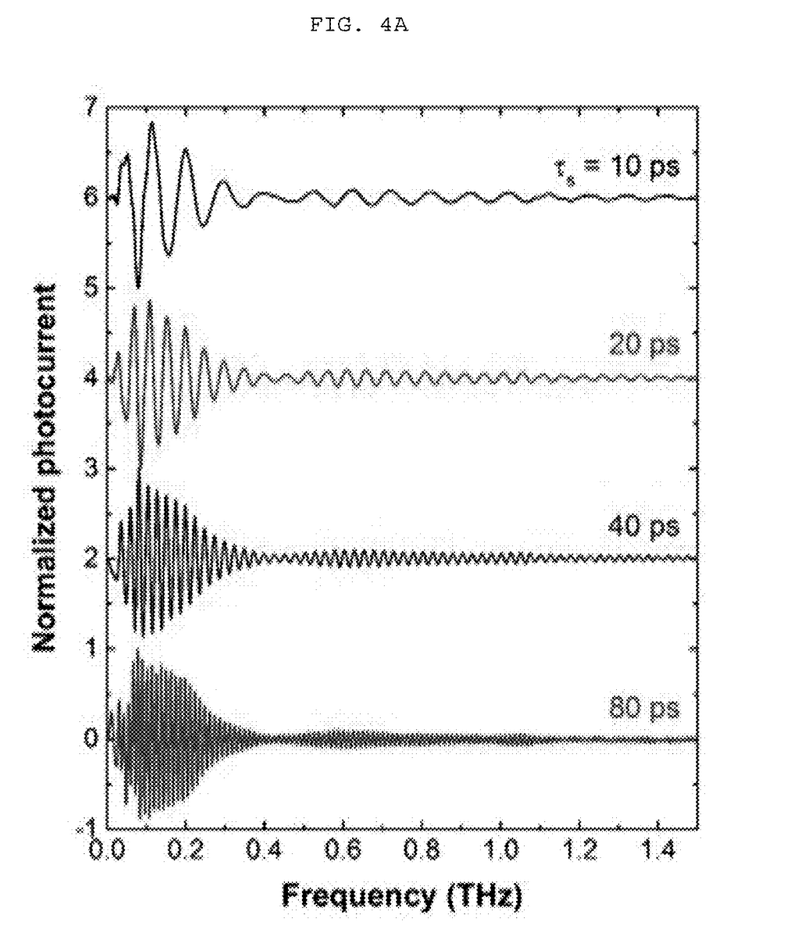
FIGS. 4A and 4B are diagrams illustrating frequency-domain data measured for various time delays and time-domain data generated by performing fast Fourier transform on the frequency-domain data.
Figure 4B:
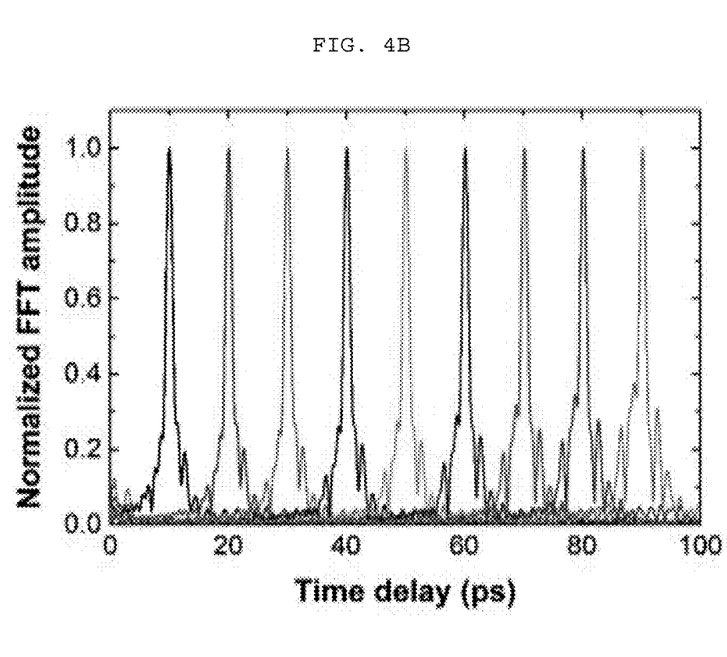

FIG. 4A is a graph illustrating frequency-domain data measured for several time delays and FIG. 4B is a graph illustrating time-domain data measured for several time delays. That is, FIGS. 4A and 4B each are a graph illustrating the frequency-domain data generated by allowing the computer 14 to convert the digital data acquired by the digitizer 13 and a graph illustrating the time-domain data generated by performing the fast Fourier transform on the frequency-domain data, for various time delays set by the variable time delay tool 6. Unlike FIG. 4A illustrating the frequency-domain data, in FIG. 4B illustrating the time-domain data generated by performing the fast Fourier transform on the frequency-domain data, a peak is generated at a position of the delayed time and therefore it may be appreciated that the time delay information may be easily extracted. The delay time occurs due to the difference between the lengths of the two optical paths from the coupler to the detector. Therefore, the time-domain data generated by performing the fast Fourier transform on the frequency-domain data may be used as the depth direction information of the sample.

Example of 3D Image Detection

Figure 5A:
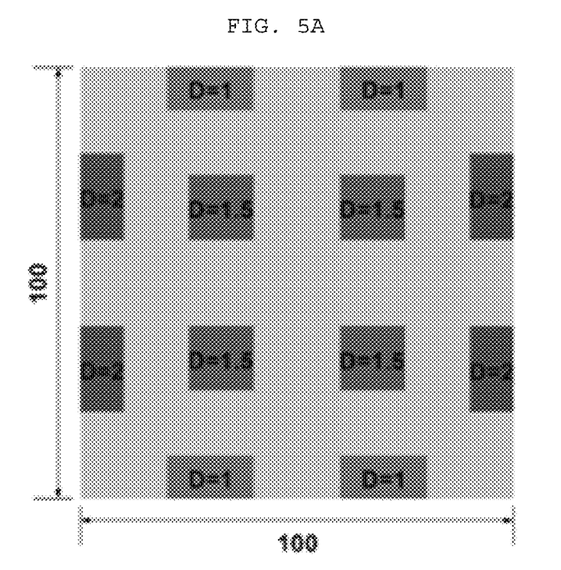
FIGS. 5A to 5C are diagrams illustrating 3D images of an actual sample detected by the high-speed 3D imaging system according to the exemplary embodiment of the present invention.
Figure 5B:
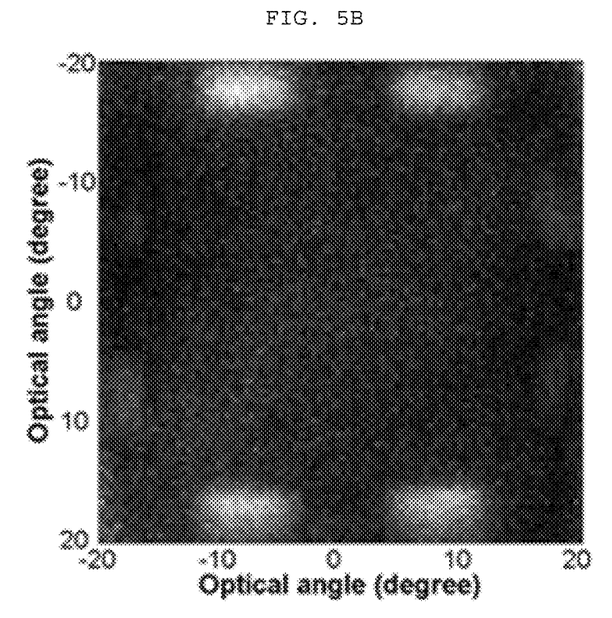
Figure 5C:
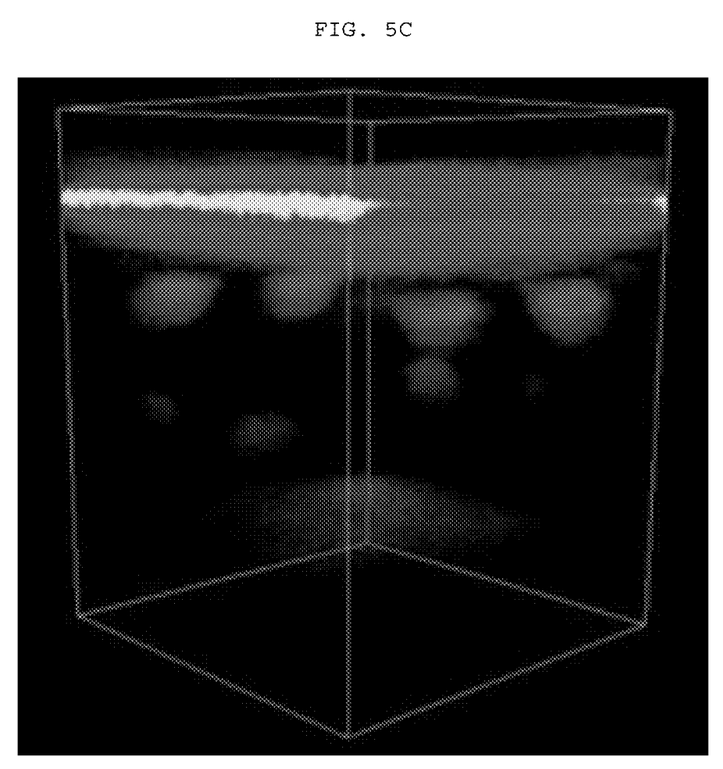

FIGS. 5A to 5C illustrate an example of 3D images of an actual sample detected by the high-speed 3D imaging system according to the exemplary embodiment of the present invention. FIG. 5A is a design diagram of a glass fiber reinforced polymer (GFRP) sample used as the sample, in which a portion marked by "D=1.5" in FIG. 5A represents a polytetrafluoroethylene (PTFE) portion included in the GFRP sample and portions marked by "D=2" and "D=1" represent portions where a layer is delaminated. That is, the sample in which other material or a delaminated layer is present was artificially manufactured according to the design of FIG. 5A and then it was experimented whether the 3D image may be accurately obtained by the system illustrated in FIG. 3. In more detail, the sample was manufactured so that a breadth, a width, and a depth of the GFRP sample each are 100 mm, 100 mm, and 3 mm, the PTFE having a thickness of 0.025 mm is present at a position marked by "D=1.5" and a depth position of 1.5 mm, and the release layer having a thickness of 0.2 mm is present at positions marked by "D=1" and "D=2" and the respective depth positions of 1 mm and 2 mm.

The sweep rate of the wavelength-swept laser is 1 kHz and the turn on/off is alternately repeated to improve the signal to noise ratio, such that 500 depth direction information (A-scan data) per second may be obtained. Positions of 100 in breadth*100 in width on 2D were measured and five depth direction information per each position were measured to be averaged and time required for the measurement is 100 seconds.

FIG. 5B illustrates the 2D (C-scan) image obtained by the experiment result, in which the 2D image was configured of peaks of each depth direction information after a front reflected signal and a rear reflected signal of the sample are removed from the depth direction information obtained at each 2D position. FIG. 5C illustrates a 3D image reconfigured by using the depth direction information obtained at each 2D position. As illustrated, the 3D image might be obtained to check whether foreign materials are present at the position corresponding to the previously known sample information. In particular, as described above, the measurement time taken to obtain the 3D detection image was only 100 seconds. That is, it was confirmed from the experiment results illustrated in FIGS. 5A to 5C that the high-speed 3D image detection using the continuous-wave THz beam scan may be realized by the system according to the exemplary embodiment of the present invention.

According to the exemplary embodiments of the present invention, it is possible to fundamentally solve the problems with the existing 3D image acquiring technologies by acquiring the 3D image for the sample using the continuous-wave THz beam which is generated from a wavelength-fixed laser and a wavelength-swept laser and of which the frequency is changed at a high speed. That is, compared to the X-ray technology that is likely to cause the damage to the biological tissue, the high-speed 3D imaging system is less likely to cause the damage to the sample to greatly improve the safety and compared to the OCT technology that may detect only the depth of several mm, the high-speed 3D imaging system may remarkably improve the detectable range in the depth direction.

Above all, according to the exemplary embodiment of the present invention, it is possible to perform the detection at a much higher speed than before. In more detail, the high-speed 3D imaging system may use the continuous-wave THz beam and acquire the depth direction information in the reflection type, and therefore compared to the existing CT technology or the transmission type 3D image acquiring type using the THz beam similar thereto, does not have to acquire the projection image at many angles. As a result, it is possible to remarkably save the measurement time. Further, the existing reflection type using the THz beam may also acquire the depth direction information on multiple points on the 2D plane while moving the sample two-dimensionally to acquire the 3D image and put together the acquired depth direction information. Therefore, the existing reflection type has a limitation of improving the speed and the precision during the physical movement of the sample. However, according to the exemplary embodiments of the present invention, it is possible to change the beam irradiation position on the 2D plane by changing the irradiation direction of the continuous-wave THz beam while fixing the sample. As a result, it is possible to detect the 3D image shape using the continuous-wave THz beam at much faster and higher precision than before by making the change speed of the beam irradiation position much faster than before and solving the problem with the reduction in precision due to the physical movement of the sample.

In addition, since the existing method performs the measurement while physically moving the sample, it is hard to detect the shape of the fixed (that is, immovable) sample, while the continuous-wave THz beam scan method according to the exemplary embodiment of the present invention may detect the shape of the immovable sample.

Further, according to the exemplary embodiment of the present invention, the high-speed 3D imaging system using the continuous-wave THz beam generated from the semiconductor laser or the optical fiber laser may be more advantageous in saving costs and miniaturization than using the pulsed-wave THz beam generated from the femtosecond pulse laser.

The present invention is not limited to the above-mentioned exemplary embodiments but may be variously applied, and may be variously modified by those skilled in the art to which the present invention pertains without departing from the gist of the present invention claimed in the claims.

What is claimed is:

1. A high-speed 3D imaging system using continuous-wave THz beam scan, comprising:
   a wavelength-fixed laser generating first laser light having a first fixed wavelength;
   a wavelength-swept laser generating second laser light having a second wavelength varying from a preset minimum wavelength to a preset maximum wavelength at a high speed for one period;
   a coupler coupling the first laser light with the second laser light to form mixed light and splitting the mixed light into first mixed light and second mixed light;
   an emitter receiving the first mixed light split from the coupler to output a continuous-wave THz beam having a frequency corresponding to a difference between a frequency corresponding to the first wavelength and a frequency corresponding to the second wavelength;
   a detector receiving the second mixed light split from the coupler and the THz beam reflected from a sample to generate a photocurrent;
   a beam splitter disposed in a propagation path of the THz beam emitted from the emitter to pass the THz beam emitted from the emitter and reflect the THz beam reflected from the sample to make the THz beam incident on the detector;
   a galvanometer scanner receiving the THz beam emitted from the emitter to adjust a direction angle of the THz beam;
   a telecentric f-θ lens irradiating the THz beam of which the angle is adjusted by the galvanometer scanner toward the sample;
   a digital pulse generator generating a trigger signal with a signal at a specific wavelength of the wavelength-swept laser;
   a first waveform signal generator applying a voltage to the emitter based on the generated trigger signal;
   a 2D scan driver controlling an angle adjustment of the galvanometer scanner based on the generated trigger signal;
   a digitizer digitalizing a reflected signal of the THz beam detected by the detector and an angle adjustment driving signal of the galvanometer scanner based on the generated trigger signal; and
   a computer receiving the digitalized reflected signal of the THz beam and the digitalized angle adjustment driving signal from the digitizer to obtain 3D shape information on the sample by analyzing the reflected signal of the THz beam to obtain depth information on a shape of the sample and analyzing the angle adjustment driving signal to obtain information on 2D position on the sample from which the reflected signal of the THz beam is generated.

2. The high-speed 3D imaging system using continuous-wave THz beam scan of claim 1, wherein the wavelength-swept laser has a wavelength sweep rate that is a value ranging from hundreds of Hz to hundreds of kHz and the one period of the wavelength-swept laser is a reciprocal number of the wavelength sweep rate.

3. The high-speed 3D imaging system using continuous-wave THz beam scan of claim 1, wherein the 2D scan driver includes:

a second waveform signal generator generating a waveform signal for driving the galvanometer scanner based on the trigger signal generated from the digital pulse generator; and at least one rotation driver using the driving waveform signal received from the second waveform signal generator to rotate the galvanometer scanner.

4. The high-speed 3D imaging system using continuous-wave THz beam scan of claim 1, further comprising:

a semiconductor optical amplifier or an optical fiber amplifier for amplifying the first laser light or the second laser light.

5. The high-speed 3D imaging system using continuous-wave THz beam scan of claim 1, further comprising:

a variable time delay tool variably time-delaying the first mixed light split from the coupler and inputting the variably time-delayed first mixed light to the emitter or variably time-delaying the second mixed light and inputting the variably time-delayed second mixed light to the detector.

6. The high-speed 3D imaging system using continuous-wave THz beam scan of claim 1, further comprising:

an amplifier amplifying a signal detected by the detector and transferring the amplified signal to the digitizer.

7. The high-speed 3D imaging system using continuous-wave THz beam scan of claim 1, wherein the digitizer digitalizes the reflected signal of the THz beam detected by the detector for one period that is a reciprocal number of a wavelength sweep rate, based on the trigger signal of the same frequency as the wavelength sweep rate generated from the digital pulse generator, in digitalizing the reflected signal of the THz beam.

8. The high-speed 3D imaging system using continuous-wave THz beam scan of claim 1, wherein to improve a signal to noise ratio of the reflected signal of the THz beam, the first waveform signal generator applies a bias voltage alternately and repeatedly turned on/off based on the trigger signal generated from the digital pulse generator to the emitter, the digitizer repeatedly digitizes the reflected signal of the THz beam for the one period and provides the digitalized reflected signal to the computer, and the computer alternately adds, subtracts, and averages the repeatedly acquired digital data.

9. The high-speed 3D imaging system using continuous-wave THz beam scan of claim 1, further comprising:

at least one off-axis parabolic mirror or lens used to collimate the THz beam emitted from the emitter or focus the THz beam reflected from the beam splitter on the detector.

10. The high-speed 3D imaging system using continuous-wave THz beam scan of claim 1, wherein the 3D imaging system is configured of a head in which the emitter, the detector, the beam splitter, the off-axis parabolic mirror or lens, the galvanometer scanner, and the telecentric f-θ lens are integrally unitized, and optical fiber-coupled generator and detector are used as the emitter and the detector and thus the head is portably formed.

* * * * *